(12) United States Patent
Adair

(10) Patent No.: US 6,753,160 B2
(45) Date of Patent: Jun. 22, 2004

(54) METHOD OF USING METALOPORPHYRINS FOR TREATMENT OF ARTERIOSCLEROTIC LESIONS

(76) Inventor: Edwin L. Adair, 317 Pagon Way, Castle Pines Village, CO (US) 80104

( * ) Notice: Subject to any disclaimer, the term of this patent is extended or adjusted under 35 U.S.C. 154(b) by 0 days.

(21) Appl. No.: 10/215,881

(22) Filed: Aug. 8, 2002

(65) Prior Publication Data

US 2003/0235531 A1 Dec. 25, 2003

Related U.S. Application Data

(63) Continuation-in-part of application No. 10/176,558, filed on Jun. 21, 2002.

(51) Int. Cl.⁷ .............................. C12Q 1/02; C12Q 1/00; G01N 33/53
(52) U.S. Cl. .............................. 435/29; 435/4; 435/968
(58) Field of Search .............................. 435/4, 968, 1.1; 424/9.1, 569

(56) References Cited

U.S. PATENT DOCUMENTS

| | | |
|---|---|---|
| 3,394,369 A | 7/1968 | Rebeiz .......................... 47/58 |
| 3,846,490 A | 11/1974 | Aronova et al. ............. 562/567 |
| 3,973,129 A | 8/1976 | Blumberg et al. ....... 250/461 B |
| 4,772,691 A | 9/1988 | Eukuda et al. ............... 540/145 |
| 4,886,831 A | 12/1989 | Morcos et al. ............... 514/456 |
| 4,897,444 A | 1/1990 | Brynes et al. .............. 525/54.1 |
| 4,905,670 A | 3/1990 | Adair ........................... 128/18 |
| 4,920,143 A | 4/1990 | Levy et al. .................. 514/410 |
| 4,977,177 A | 12/1990 | Bommer et al. ............. 514/410 |
| 4,997,639 A | 3/1991 | Aizawa et al. .................. 424/9 |
| 5,026,368 A | 6/1991 | Adair ........................... 606/15 |
| 5,043,101 A | 8/1991 | Gordon ................... 252/408.1 |
| 5,079,262 A | 1/1992 | Kennedy et al. ............. 514/561 |
| 5,087,636 A | 2/1992 | Jamieson et al. ........... 514/410 |
| 5,117,466 A | 5/1992 | Buican et al. .................. 362/6 |
| 5,122,453 A | 6/1992 | Martin et al. ............... 435/7.24 |
| 5,143,054 A | 9/1992 | Adair ........................... 128/18 |
| 5,149,708 A | 9/1992 | Dolphin et al. ............. 514/410 |
| 5,211,938 A | 5/1993 | Kennedy et al. ............. 424/7.1 |
| 5,234,940 A | 8/1993 | Kennedy et al. ............ 514/410 |
| 5,251,613 A | 10/1993 | Adair ............................ 128/6 |
| 5,270,171 A | 12/1993 | Cercek et al. ................ 435/29 |
| 5,283,255 A | 2/1994 | Levy et al. .................. 514/410 |
| 5,308,608 A | 5/1994 | Dolphin et al. ................ 424/9 |
| 5,308,861 A | 5/1994 | Aizawa ....................... 514/410 |

(List continued on next page.)

FOREIGN PATENT DOCUMENTS

| | | |
|---|---|---|
| EP | 0 277 837 | 10/1988 |
| JP | 04330013 A | 11/1992 |
| JP | 408295639 A * | 11/1996 |
| WO | WO 02/096366 | 12/2002 |

OTHER PUBLICATIONS

Abstract, Mu Y, et al., "P–S–D–007 Luminescence in the Diagnosis of Exfollative Cells from Malignant Tumors", X–P–0021614131, vol. 9, No. 4, 1987, pp. 258–259.

(List continued on next page.)

Primary Examiner—Louise N. Leary
(74) Attorney, Agent, or Firm—Sheridan Ross P.C.

(57) ABSTRACT

A method for diagnosis and treatment of arteriosclerotic lesions is provided wherein the method is characterized by introducing a chemical compound to the patient, the compound being a complex of a photosensitive portion, and a radioactive portion. Cells which exhibit an affinity for the porphyrin element indicate sites of plaque buildup. The radioactive portion within the compound allows tomographic scanning as well as simultaneous radiation treatment. The complexed compound can be introduced to the patient a desired number of times to provide the necessary radiation treatment and ongoing monitoring of plaque removal. Further observation or treatment may be conducted through a fluorescence guided endoscopic procedure.

25 Claims, 1 Drawing Sheet

U.S. PATENT DOCUMENTS

| | | | | |
|---|---|---|---|---|
| 5,391,547 | A | 2/1995 | Cole et al. | 514/184 |
| 5,399,583 | A | 3/1995 | Levy et al. | 514/410 |
| 5,418,169 | A | 5/1995 | Crissman et al. | 436/94 |
| 5,422,093 | A | 6/1995 | Kennedy et al. | 424/9.61 |
| 5,441,531 | A | 8/1995 | Zarate et al. | 607/90 |
| 5,554,505 | A | 9/1996 | Hajek et al. | 435/721 |
| 5,556,764 | A | 9/1996 | Sizto et al. | 435/7.24 |
| 5,591,422 | A | 1/1997 | Hemmi et al. | 424/9.362 |
| 5,605,805 | A | 2/1997 | Verwer et al. | 435/7.24 |
| 5,616,342 | A | 4/1997 | Lyons | 424/450 |
| 5,627,040 | A | 5/1997 | Bierre et al. | 435/7.24 |
| 5,652,114 | A | 7/1997 | Chu et al. | 435/7.23 |
| 5,773,609 | A | 6/1998 | Robinson et al. | 540/145 |
| 5,955,490 | A | 9/1999 | Kennedy et al. | 514/410 |
| 5,993,774 | A | 11/1999 | Archer et al. | 424/1.65 |
| 6,004,531 | A | 12/1999 | Archer et al. | 424/1.65 |
| 6,190,877 | B1 * | 2/2001 | Adair | 435/29 |
| 6,235,767 | B1 | 5/2001 | Kelly et al. | 514/410 |
| 6,350,431 | B1 | 2/2002 | Snow et al. | 424/9.6 |
| 6,358,989 | B1 | 3/2002 | Kunz et al. | 514/411 |
| 6,387,350 | B2 | 5/2002 | Goldenberg | 424/1.57 |
| 6,395,016 | B1 | 5/2002 | Oron et al. | 607/88 |
| 6,422,988 | B1 | 7/2002 | Bradshaw et al. | 600/3 |
| 6,422,989 | B1 | 7/2002 | Hektner | 600/3 |

OTHER PUBLICATIONS

Abstract, Schwartz, G., et al., "Selected Amino Acridines as Fluorescent Probes in Cytochemistry in General and in the Detection of Cancer Cells in Particular", *Analytical and Quantitative Cytology*, vol. 4, No. 1, 1982, pp. 44–54.

Abstract, Gardiner, R.A., et al., "Abnormal prostatic cells in ejaculates from men with prostatic cancer: A preliminary report", *British Journal of Urology*, vol. 78, No. 3, 1998, pp. 414–418.

Abstract, Bologna, M., et al., "Improved tissue culture method for the study of prostatic carcinoma: A significant diagnostic tool.", *Pathology Research and Practice*, vol. 191, No. 9, 1995, pp. 899–903.

Abstract, Sauter, E.R., et al., "Nipple aspirate fluid: A promising non–invasive method to identify cellular markers of breast cancer risk", *British Journal of Cancer*, vol. 76, 1997, pp. 494–501.

Abstract, Sugiyama, M., et al., "Non–invasive detection of bladder cancer by identification of abnormal CD44 proteins in exfoliated cancer cells in urine", Abstract, *Clinical Molecular Patholgy*, 1995, vol. 48, pp. M142–M147.

Nyamekye et al.: "Photodynamic Therapy of Normal and Balloon–Injured Rat Carotid Arteries Using 5–Amino–Levulinic Acid"; *Circulation*, vol. 91, No. 2, Jan. 15, 1995, pp. 417–425.

Peng et al., "5–Aminolevulinic Acid–Based Photodynamic Therapy"; *American Cancer Society*; 1997; pp. 2282–2305.

Berg et al.; "The Influence of Iron Chelators On the Accumulation of Protoporphyrin IX in 5–Aminolaevulinic Acid–Treated Cells"; *British Journal of Cancer*; 1996; pp. 688–697.

Noodt et al.; "Apoptosis and Necrosis Induced With Light and 5–Aminolaevulinic Acid–Derived Protoporphyrin IX"; *Flow Cytometry*;1996; pp. 22–29.

Malik et al.; "Destruction of Erythroleukaemic Cells by Photoactivation of Endogenous Porphyrins"*British Journal of Cancer*, 1987; 56; pp. 589–595.

Leon et al.; "Localized Intracoronary Gamma–Radiation Therapy to Inhibit the Rcurrence of Restenosis After Stenting"; *The New England Journal of Medicine*; Jan. 25, 2001; 344(4); pp. 250–256.

Verin et al.; "Endoluminal Beta–Radiation Therapy for the Prevention of Coronary Restenosis After Balloon Angioplasty"; *The New England Journal of Medicine*; Jan. 25, 2002; 344(4); pp. 243–249.

Abstract: Leunig et al.; "Fluorescence Photodetection of Neoplastic Lesions in the Oral Cavity Following Topical Application of 5–Aminolevulinic Acid", *Laryngo–Rhino–Otologie*; vol. 75, No. 8, Aug. 1996; pp. 459–464.

Artemov et al., *Cancer Res.*, 61:3039–3044 (2001).

Fiel et al., *Cancer Letters*, 40:23–32 (1988).

Furnanski and Longley, *Cancer Res.*, 48:4604–4610 (1988).

Harisinghani et al., *N. Engl. J. Med.*, 348(25):2491–2499 (2003).

Koenig et al., *Magnetic Resonance in Medicine*, 4:252–260 (1987).

Lyon et al., *Magnetic Resonance in Medicine*, 4:24–33 (1987).

Rosenthal et al., *Clin. Cancer Res.*, 5:739–745 (1999).

van Zijl et al., *Acta Radiologica*, 374(supp):75–79 (1990).

Fimsu et al.: "Cu Labelling of Hematoporphyrin Derivative for Non–Invasive In–Vivo Measurements of Tumour Uptake" *Porphyin Localization and Treatment of Tumors*: 1984 Alan R. Liss, Inc.: pp. 629–636.

Kulkami et al.; "Radio Indium and Gallium Labeled Porphyrins for Medical Imaging"; AIP Conference Proceedings; 2001, 837–840.

* cited by examiner

METHOD OF USING METALOPORPHYRINS FOR TREATMENT OF ARTERIOSCLEROTIC LESIONS

CROSS REFERENCE TO RELATED APPLICATIONS

This application is a continuation-in-part of co-pending application Ser. No. 10/176,558, filed on Jun. 21, 2002 entitled Method of Cancer Screening Primarily Utilizing Non-Invasive Cell Collection, Fluorescence Detection Techniques, and Radio Tracing Detection Techniques, which is incorporated herein in its entirety by this reference.

FIELD OF THE INVENTION

This invention relates to use of radiopharmaceuticals in the treatment of arteriosclerotic lesions in blood vessels, and more particularly, to the use of metaloporphyrins wherein a porphyrin is complexed with a radioactive metal for targeted delivery of radiation to arteriosclerotic lesions.

BACKGROUND OF THE INVENTION

It is known that certain types of obstructions in arteries may be due, in part, to arteriosclerotic plaques. These plaques typically result from the proliferation of smooth muscle cells and associated fibrous tissue which invades the wall and lining cells (intima) of the artery. While the reasons for the smooth muscle and fibrous cell proliferation in the arterial walls is not completely understood, this proliferation is not generally considered to be neoplastic in origin, in spite of the fact that regeneration of plaque can take place very rapidly, sometimes within a few months of total removal by coronary endarterectomy.

Management of arteriosclerotic stenosis by balloon angioplasty is a common treatment method; however, the effectiveness of such treatment is limited by restenosis. Restenosis occurs in about 30% to 50% of patients having undergone angioplasty. Fibrocellular intimal hyperplasia is a main cause of such restenosis which arises from proliferation of smooth muscle cells in the intimal layer.

Porphyrins are a large class of typically red or purple fluorescent crystalline pigments, with natural or synthetic origin, having in common a substituted aromatic macrocyclic ring consisting of four pyrrole-type residues, linked together by four methine bridging groups. It is recognized that smooth muscle cells which proliferate in arteries have a distinct affinity for various porphyrin compounds such as HPD, photofrin, photofrin II, and a long list of other porphyrin compounds. A proliferating smooth muscle cell will take up such porphyrin compounds much in the same manner as cells which are either dysplastic or overtly malignant. Because these cells become sensitized by these porphyrin compounds, they are capable of responding to both photo-detection and photo-destruction when proper frequencies of light are administered. Use of this "photodynamic" therapy in the management of angioplasty restenosis in patients is described in *Photodynamic Therapy of Normal and Balloon Injured Rat Carotid Arteries Using 5-Amino-Levulinic Acid*, Circulation, 91(2):417–25 (1995), incorporated herein by this reference in its entirety for disclosing basic procedures for photodynamic therapy of arteriosclerotic abnormalities.

Although many physicians and researchers are familiar with photodynamic therapy and many have used such procedures in the laboratory, few have become advocates of the therapy because of the severe limitations imposed by the use of porphyrins which utilize light frequencies that do not penetrate, and are therefore impossible to deliver to any significant depth in tissue. The light frequencies required for photo detection generally range between 380–420 nm, and the resulting fluorescence is typically in the range of 635 nm. Because of these wavelengths, penetration of the light source is restricted to tissue of minimal depth in the body. Accordingly, without surgical intervention, phototherapy is not capable of effectively reaching arteriosclerotic lesions.

As also understood by those skilled in the art, photodynamic therapy has been used for treatment of various cancers. Examples of references which disclose use of photodynamic therapy for treatment of cancer include the U.S. Pat. Nos. 5,087,636 and 5,211,938.

Another significant, well known method for treatment of arteriosclerotic abnormalities includes localized intercoronary radiation therapy. This therapy is reviewed in *Localized Intercoronary Gamma Radiation Therapy to Inhibit the Recurrence of Restenosis after Stenting, and Endoluminal Beta Radiation Therapy for the Prevention of Coronary Restenosis after Balloon Angioplasty*, The New England Journal of Medicine, 344(4)243–56 (2001). The studies reported therein indicate significantly lowered rates of clinical and angiographic restenosis following radiation therapy.

There are also a number of references which further disclose radiation therapy for arteriosclerotic abnormalities including U.S. Pat. Nos. 6,422,989; 6,422,988; 6,395,016; 6,387,350; 6,358,989; and 6,235,767.

Finally, there is a known treatment for cancer which utilizes metaloporphyrins to deliver site selective radiation therapy. More specifically, U.S. Pat. No. 5,391,547 discloses a method for using porphyrins to detect lung cancer by the use of tetra-aryl porphyrins. The porphyrins are used as fluorescent tracers for cancers of the lung. The porphyrins are complexed with $^{64}$Cu or $^{67}$Cu. Thus, the complex can be used as radiotracers as well. The $^{67}$Cu provides a source of beta radiation for selective destruction of lung malignancies as well as gamma radiation useful for image analysis, as by a single photon emission computed tomography (SPECT). The $^{64}$Cu as a positron emitter, may be used for radiotracing wherein positron emission tomography (PET) techniques can be used to locate the malignant tissue.

While the aforementioned radiation treatments for arteriosclerotic abnormalities have shown some promise, one significant drawback to known procedures is the inability to effectively localize the radio compounds in the targeted tissue. Furthermore, such radiation treatment is typically done after there has already been an interventional procedure conducted, such as balloon angioplasty or stent emplacement. Thus, such radiation is primarily used as a follow-up treatment and not an initial treatment of arteriosclerotic abnormalities.

While photodynamic therapy also has been proven to be effective in prevention of arteriosclerosis, photodynamic therapy in practice is extremely difficult to incorporate because an illuminating catheter must be delivered to the damaged arterial locations and even after the catheter has reached the site to be treated, normal blood flow through the arteries further complicates the ability to deliver an effective intensity of light to the targeted tissue.

Therefore, while photodynamic therapy and radiation treatment can potentially be effective, there is still a need for a non-interventional procedure for treatment of arteriosclerotic abnormalities which provides not only an initial screening or diagnosis, but also may be simultaneously used for actual treatment of the affected blood vessels to reduce and destroy plaque and prevent or eliminate restenosis.

SUMMARY OF THE INVENTION

The present invention provides a method for diagnosis, visualization and treatment for arteriosclerotic abnormalities. The method is non-invasive and can be utilized to remove arteriosclerotic plaque at any inter-arterial site in the body. This new modality of treatment can be directed at arteries which have had no previous surgical intervention, as well as those sites which have been previously treated such as by balloon angioplasty or stent emplacement.

The present invention makes use of porphyrin compounds complexed with various metals such as silver (Ag), aluminum (Al), cadmium (Cd), cobalt (Co), chromium (Cr), copper (Cu), iron (Fe), gadolinium (Gd), indium (In), lutetium (Lu), magnesium (Mg), manganese (Mn), nickel (Ni), palladium (Pd), platinum (Pt), rhodium (Rh), ruthenium (Ru), scandium (Sc), silicon (Si), tin (Sn), titanium oxide (TiO), vanadium oxide (VO), ytterbium (Yb) and zinc (Zn). These complexes are generally categorized as metaloporphyrins meaning a porphyrin moiety having a chelated radioactive isotope of a metal atom. These metaloporphyrins are further processed so that the metal is in the form of a radioactive isotope. The resulting radioactive metaloporphyrins thereby constitute radiopharmaceuticals that can be intravenously introduced to the patient. The affinity of the smooth muscle cells and fibrous tissue (plaque) for porphyrins results in selective uptake of the radioactive metaloporphyrin, thereby effecting targeted delivery of therapeutic radiopharmaceuticals to plaque lesions. In the instance of elemental copper chelated by the porphyrin, the copper can be transformed to radioactive $^{67}Cu$. In this way, introduction of the metaloporphyrin radiopharmacuetical to the patient is an effective means of targeted or site-selective deliver of measured radiation therapy to the targeted arteriosclerotic tissue. Additionally, these metaloporphyrin complexes still provide the ability to simultaneously conduct fluorescence detection and phototherapy if desired. Also, the metaloporphyrins provide the ability for observation of the areas of plaque buildup through PET scanning (for example, through use of $^{64}Cu$) or SPECT scanning (for example, through use of $^{67}Cu$). Metaloporphyrins complexed with $^{67}Cu$, also provide a source of beta radiation for the selective destruction of plaque sites.

Accordingly, the method of the invention provides a non-invasive (non-surgical) procedure, and also provides various options for initial diagnosis and treatment of plaque buildup. The natural affinity of the proliferating tissues for the porphyrin compounds provides an effective means for delivering radiation to the affected tissue.

DETAILED DESCRIPTION OF THE INVENTION

Figure 1:
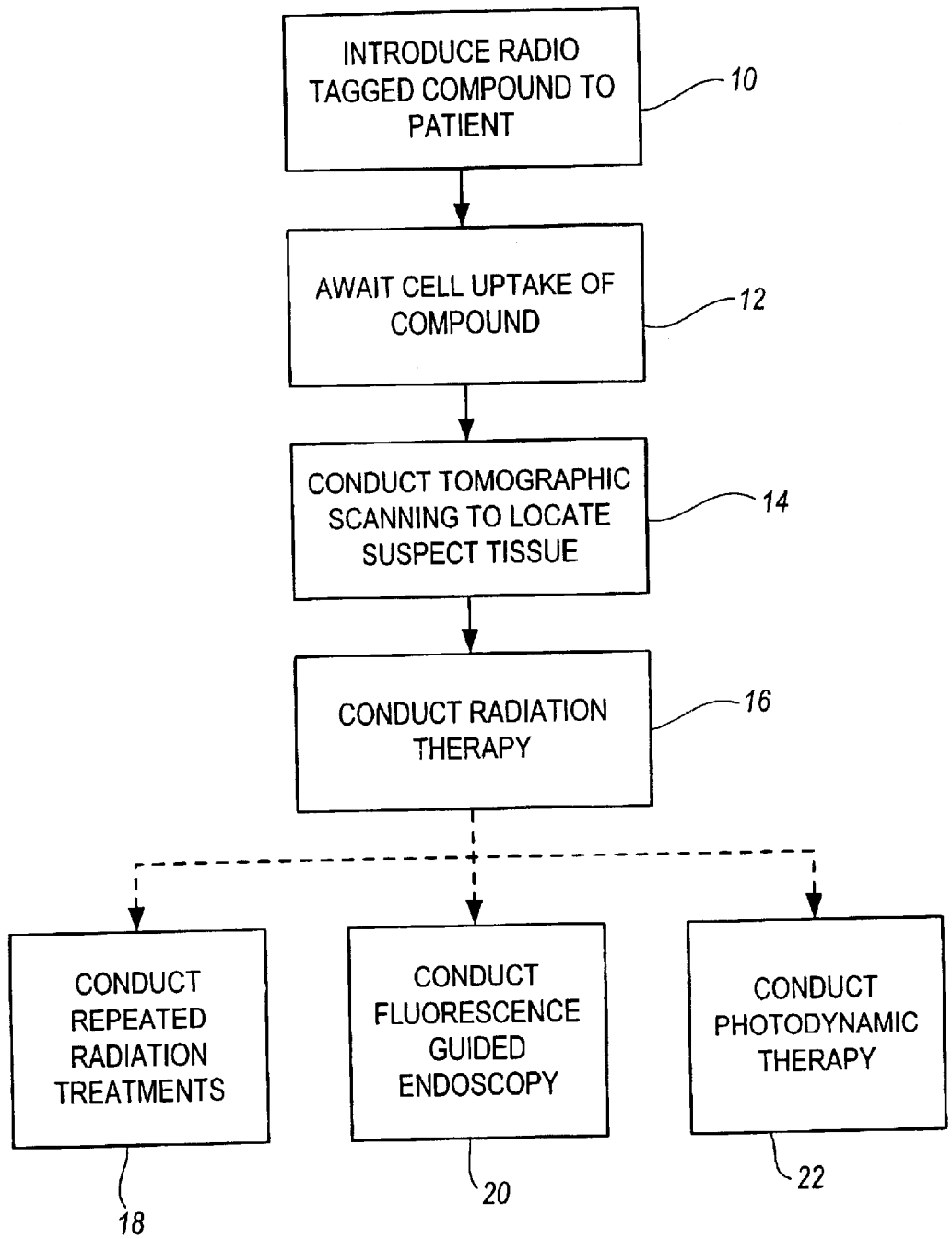
FIG. 1 is a simplified flow diagram illustrating the major steps in the method by use of the porphyrin complexes for radio tracing through scanning and radiation therapy.

In addition to use of known porphyrins, a number of additional photo-sensitive compounds may be complexed with selected metals. These additional compounds include, without limitation, 5-amino levulenic acid (5-ALA), protoporphyrin IX, TCPP, hematoporphyrin derivative, photofrin, photofrin II, uroporphyrin, coproporphyren, tetraphenylporphinesulfonate (TPPS) and tetraporphen (4, N-methylulpyridil) (TMPP). Each of these photosensitive compounds, to include the below listing of metaloporphyrins are available from Frontier Scientific (formerly Porphyrin Products), of Logan Utah. These commercially available metaloporphyrins are further treated to convert the elemental metals to radioactive isotopes. Conversely, these radioactive metaloporphyrins useful as radiopharmaceutical agents may be formed by purchasing or isolating radioactive metals of interest which are then combined with the desired porphyrin molecules to form radioactive metaloporphyrins. U.S. Pat. No. 5,391,547 is hereby incorporated by reference for purposes of disclosing the use of metaloporphyrins and the methods by which metaloporphyrins are manufactured and combined with metal isotopes. Some of the metaloporphyrins suitable for use in the present invention that are commercially available through Frontier Scientific include Protoporphyrin IX and derivatives thereof including Protoporphyrin IX Dimethyl Ester, Protoporphyrin IX Acid, and Protoporphyrin IX Na Salt; Porphine; Octaethylporphine; Hematoporphyrin IX and derivatives thereof including Hematoporphyrin D and Hematoporphyrin IX Dimethyl Ester; Etioporphyrin and Etioporphyrin I; meso-Tetraphenylporphine and derivatives thereof including meso-Tetra (N-methyl-4-Pyridyl) porphine, meso-Tetra (4-Pyridyl) porphine, meso-Tetra (4-sulfonatophenyl) porphine and meso-Tetra (4-carboxyphenyl) porphine; Coproporphyrin I and Coproporphyrin III; Deuteroporphyrin IX and derivatives thereof including Deuteroporphyrin IX Bis Glycol and Deuteroporphyrin Disulfonic Acid; Mesoporphyrin IX; Tetra Tosylate; Uroporphyrin I; and Isohematoporphyrin IX. Each of these porphyrins may be complexed with a radioactive isotope as desired.

Now referring to FIG. 1, the first step in the method is to introduce the radio tagged porphyrin compound to a patient having been diagnosed with, or having a suspected plaque buildup. The administration may be conducted by intravenous administration of the porphyrin radiopharmaceutical or may be conducted through a catheter specifically placed to direct the porphyrin radiopharmaceutical to a specific arterial site within the patient. This is shown as step 10. The necessary period of time is then given to allow cell uptake of the compound, shown at block 12. In block 14, tomographic scanning can be conducted to determine sites of plaque buildup. If no appreciable arteriosclerotic abnormalities are observed, then the procedure is complete; however, if arteriosclerotic abnormalities are found, delivery of the radio tagged compound results in selective ionizing radiation of the intra-arterial tissue occurring, shown at step 16. As necessary, step 16 can be repeated by repeated introduction of the radio-tagged porphyrin compound or the further introduction of a different radio-tagged porphyrin compound, thereby enabling a selective number of radiation treatments to take place in order to destroy the targeted tissue. Repeated radiation treatment is shown as optional step 18. Although step 16 is shown as a separate step, it shall be understood that the radiation treatment takes place simultaneously each time a patient is provided the radio-tagged porphyrin compound, even with the initial administration. Additionally, for each necessary radiation therapy treatment, the particular metaloporphyrin can be dosed with the desired amount and type of radioactive material thereby providing adjustability for delivering the desired amount of radiation and type of radiation. As also mentioned above, if it were desired to actually visualize the destruction of the targeted tissue, an interventional procedure could take place such as by introduction of a catheter to the targeted area. Using photo-detection methodology, the tissue can be observed to confirm the results of the treatment. This optional step is shown as step 20. Additionally, photo-dynamic therapy could also be conducted if an interventional procedure was performed to record and/or confirm the results of the procedure. This is shown as optional step 22. Further, an interventional procedure such as balloon angioplasty or stent emplacement can be augmented by the use of the porphyrin radiopharmaceuticals of the present invention. By this means, the porphyrin radiopharmaceuticals are administered prior to or after performing the interventional procedure to enhance the benefits gained from the interventional therapy and to decrease or eliminate the rate of restenosis seen following these procedures.

The ability to simultaneously conduct a non-interventional diagnostic procedure and to simultaneously provide treatment is a very clear advantageous use of metaloporphyrins in diagnosing and treating arteriosclerotic abnormalities. The porphyrin which is used as a carrier for delivering the radiation to the patient also helps to localize the radioactive material in the tissue that requires the treatment. As described in U.S. Pat. No. 5,391,547, these porphyrin-based therapeutic agents may additionally localize to cancers of the lung. Thus, as an additional benefit of the therapeutic treatment of arteriosclerotic plaque, these metaloporphyrin radiopharmaceuticals may additionally detect and treat any cancerous tissue present in patients in need of treatment for arteriosclerotic plaque.

Referring specifically to the use of isotopes of copper, a metaloporphyrin complexed with $^{67}$Cu provides not only the ability to conduct visualization through SPECT scanning, but the $^{67}$Cu also provides beta radiation for purposes of providing radiation therapy. $^{64}$Cu is a positron emitter which does not allow for radiation treatment; however, $^{64}$Cu can be utilized for purposes of conducting PET scanning. Therefore, it is also contemplated within the spirit and scope of the invention to provide metaloporphyrins for tomographic scanning, and other metaloporphyrins for radiation treatment. Thus, it is also contemplated that the metaloporphyrin complexes may be specifically designed to produce gamma, positron, and beta emissions as desired to enable the desired type of tomographic scanning, as well as radiation therapy. Moreover, it is possible to use a first radioactive metaloporphyrin for diagnosis or visualization of arteriosclerotic plaque followed by the use of a second radioactive metalophophyrin for treatment of any arteriosclerotic tissue found with the first radioactive metalophophyrin. In this way, the porphyrin and/or the radioactive isotope may be chosen due to their respective suitability for the procedure performed; either detection or destruction of the arteriosclerotic tissue. For example, the initial diagnosis and imaging may be conducted with a $^{64}$Cu-containing porphyrin while any subsequent treatment of arteriosclerosis may be performed with $^{67}$Cu-containing porphyrin. Further to modifying or selecting the porphyrin and intercalated radioactive isotope for specific procedures, the porphyrin and isotope may be selected for repetition of the therapy. Finally, it is contemplated that the therapy may also be modified in number and frequency of repetitive treatments based on the porphyrin and/or radioactive isotope used.

This application has been described with respect to a preferred embodiment; however, various modifications can be made which fall within the spirit and scope of the invention.

What is claimed is:

1. A method of screening and treatment of arteriosclerotic disease, said method comprising the steps of:
   introducing a complexed compound to a patient for cell uptake of the compound, the compound comprising a first portion which includes a photosensitive component, and a second portion comprising a radioactive marker;
   conducting tomographic scanning of the patient to determine whether targeted cells in the patient have demonstrated an affinity for the photosensitive compound thereby indicating the presence of plaque buildup; proportional to arteriosclerotic disease; and
   conducting radiation therapy by the second portion of the compound which results in selective ionizing radiation exposure.

2. A method, as claimed in claim 1, wherein:
   said first portion of said compound is selected from the group consisting of 5-ALA, protoporphyrin IX, TCPP, hematoporphyrin derivative; photofrin, uroporphyrin, coproporphyrin, TPPS, and TMPP; and
   said second portion of said compound is selected from the group consisting of radioisotopes of copper which may be complexed with said first portion.

3. A method, as claimed in claim 2, wherein said radioisotope of copper is $^{67}$Cu.

4. A method, as claimed in claim 1, further comprising the step of:
   selecting the type of radioactive marker to match a type of radiation treatment best suited for treatment of a disease.

5. A method, as claimed in claim 1, further comprising the step of:
   introducing the complexed compound again to the patient to achieve further radiation therapy; and
   conducting tomographic scanning to view treatment results.

6. A method, as claimed in claim 1, further comprising the step of:
   introducing the complexed compound wherein the second portion is selectively dosed to deliver a desired amount of radiation.

7. A method, as claimed in claim 6, further including the step of adjusting the type and dosage of the second portion to provide effective therapy.

8. A radiopharmaceutical composition for the visualization, diagnosis or treatment of arteriosclerosis comprising a porphyrin complexing a radiation-emitting metal and a pharmaceutical excipient.

9. The radiopharmaceutical composition of claim 8, wherein the porphyrin is selected from the group consisting of Protoporphyrin IX and derivatives thereof; Porphine; Octaethylporphine; Hematoporphyrin IX and derivatives thereof; Etioporphyrin; Etioporphyrin I; meso-Tetraphenylporphine and derivatives thereof; Coproporphyrin I; Coproporphyrin III; Deuteroporphyrin IX; Mesoporphyrin IX; Tetra Tosylate; Uroporphyrin I; and Isohematoporphyrin IX.

10. The radiopharmaceutical composition of claim 8, wherein the radiation-emitting metal is a radioactive isotope of a metal selected from the group consisting of silver, aluminum, cadmium, cobalt, chromium, copper, iron, gadolinium, indium, lutetium, magnesium, manganese, nickel, palladium, platinum, rhodium, ruthenium, scandium, silicon, tin, titanium oxide, vanadium oxide, ytterbium and zinc.

11. A method of visualizing an arteriosclerotic region in an individual comprising:
   (a) administering a radiopharmaceutical comprising a porphyrin complexing a gamma radiation-emitting metal to an individual, and
   (b) detecting the gamma radiation emitted from within the individual to create an image of an arteriosclerotic region within the individual.

12. The method of claim 11, wherein the porphyrin is selected from the group consisting of Protoporphyrin IX and derivatives thereof, Porphine; Octaethylporphine; Hematoporphyrin IX and derivatives thereof, Etioporphyrin; Etioporphyrin I; meso-Tetraphenylporphine and derivatives thereof; Coproporphyrin I; Coproporphyrin III; Deuteroporphyrin IX; Mesoporphyrin TX; Tetra Tosylate; Uroporphynn I; and Iso-hematoporphyrin IX.

13. The method of claim 11, wherein the radiation-emitting metal is a radioactive isotope of a metal selected from the group consisting of silver, aluminum, cadmium, cobalt, chromium, copper, iron, gadolinium, indium, lutetium, magnesium, manganese, nickel, palladium, platinum, rhodium, ruthenium, scandium, silicon, tin, titanium oxide, vanadium oxide, ytterbium and zinc.

14. The method of claim 11, wherein the detecting step comprises positron emission tomography (PET) scanning.

15. The method of claim 11, wherein the detecting step comprises single photon emission computed tomography (SPECT) scanning.

16. A method of diagnosing arteriosclerosis in an individual comprising:

(a) administering a radiopharmaceutical comprising a porphyrin complexing a gamma radiation-emitting metal to an individual, (b) detecting the gamma radiation emitted from within the individual, and (c) comparing the detected gamma radiation reading from the individual with reference readings wherein comparison to reference readings is indicative of the presence of arteriosclerosis in an individual.

17. The method of claim 16, wherein the detecting step is selected from the group consisting of PET scanning and SPECT scanning, and wherein the reference readings are PET or SPECT scans of individuals known to have arteriosclerosis.

18. The method of claim 16, wherein the detecting step is selected from the group consisting of PET scanning and SPECT scanning, and wherein the reference readings are PET or SPECT scans of individuals in which arteriosclerosis is absent.

19. The method of claim 16, wherein the porphyrin is selected from the group consisting of Protoporphyrin IX and derivatives thereof; Porphine; Octaethylporphine; Hematoporphyrin IX and derivatives thereof; Etioporphyrin; Etioporphyrin I; meso-Tetraphenylporphine and derivatives thereof; Coproporphyrin I; Coproporphyrin III; Deuteroporphyrin TX; Mesoporphyrin LX; Tetra Tosylate; Uroporphyrin I; and Iso-hematoporphyrin IX.

20. The method of claim 16, wherein the gamma radiation-emitting metal is a radioactive isotope of a metal selected from the group consisting of silver, aluminum, cadmium, cobalt, chromium, copper, iron, gadolinium, indium, lutetium, magnesium, manganese, nickel, palladium, platinum, rhodium, ruthenium, scandium, silicon, tin, titanium oxide, vanadium oxide, ytterbium and zinc.

21. A method of treating arteriosclerosis in an individual comprising administering a therapeutically-effective amount of a radiopharmaceutical comprising a porphyrin complexing a radiation-emitting metal to an individual.

22. The method of claim 21, wherein the radiation-emitting metal is a beta radiation-emitting metal.

23. The method of claim 21, wherein the radiation-emitting metal is a gamma radiation-emitting metal.

24. The method of claim 21, wherein the porphyrin is selected from the group consisting of Protoporphyrin IX and derivatives thereof; Porphine; Octaethylporphine; Hematoporphyrin IX and derivatives thereof; Etioporphyrin; Etioporphyrin I; meso-Tetraphenylporphine and derivatives thereof; Coproporphyrin I; Coproporphyrin III; Deuteroporphyrin DC; Mesoporphyrin IX; Tetra Tosylate; Uroporphyrin I; and Iso-hematoporphyrin DC.

25. The method of claim 21, wherein the radiation-emitting metal is a radioactive isotope of a metal selected from the group consisting of silver, aluminum, cadmium, cobalt, chromium, copper, iron, gadolinium, indium, lutetium, magnesium, manganese, nickel, palladium, platinum, rhodium, ruthenium, scandium, silicon, tin, titanium oxide, vanadium oxide, ytterbium and zinc.

* * * * *

UNITED STATES PATENT AND TRADEMARK OFFICE
CERTIFICATE OF CORRECTION

PATENT NO. : 6,753,160 B2
DATED : June 22, 2004
INVENTOR(S) : Edwin L. Adair

It is certified that error appears in the above-identified patent and that said Letters Patent is hereby corrected as shown below:

Title page,
Item [56], References Cited, U.S. PATENT DOCUMENTS, please add the following:
-- 6,566,517    5/20/03    Miura et al.    540/145 --
OTHER PUBLICATIONS, please amend as follows:
Please delete "Fumanski" and insert -- Furmanski -- therein.
Please delete "Fimsu et al." and insert -- Firnau et al. -- therein.

Column 6,
Line 6, please delete "buildup;" and insert -- buildup -- therein.
Line 14, please delete "derivative;" and insert -- derivative -- therein.

Column 7,
Lines 3 and 4, please delete "thereof," and insert -- thereof; -- therein.
Line 7, please delete "Uroporphynn" and insert -- Uroporphyrin -- therein.

Column 8,
Lines 6-7, please delete "Deuteroporphyrin TX; Mesoporphyrin LX;" and replace with
-- Deuteroporphyrin IX; Mesoporphyrin IX; -- therein.
Lines 30-31, please delete "Deuteroporphyrin DC;" and replace with -- Deuteroporphyrin IX -- therein.
Line 32, please delete "Iso-hematoporphyrin DC" and replace with -- Iso-hematoporphyrin IX -- therein.

Signed and Sealed this

Thirtieth Day of November, 2004

JON W. DUDAS
*Director of the United States Patent and Trademark Office*